(12) United States Patent
Wallace et al.

(10) Patent No.: US 8,377,712 B2
(45) Date of Patent: Feb. 19, 2013

(54) COMPOSITIONS AND METHODS FOR THE DETECTION OF CHEMICAL WARFARE AGENTS

(75) Inventors: Karl J. Wallace, Hattiesburg, MS (US); Eric V. Anslyn, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1820 days.

(21) Appl. No.: 11/609,202

(22) Filed: Dec. 11, 2006

(65) Prior Publication Data

US 2012/0122228 A1    May 17, 2012

Related U.S. Application Data

(60) Provisional application No. 60/748,912, filed on Dec. 9, 2005.

(51) Int. Cl.
*G01N 21/76* (2006.01)
(52) U.S. Cl. .............................. 436/172; 250/458.1
(58) Field of Classification Search .................. None
See application file for complete search history.

(56) References Cited

PUBLICATIONS

Irngartinger, H. et al. Synthesis of Isoxazolo[60]fullerenes with dumb-bell-type structure and atropisomeric properties, 1999, Eur. J. Org. Chem. pp. 2087-2092.*

Zhang et al., "Fluorescent Detection of Chemical Warfare Agents: Functional Group Specific Ratiometric Chemosensors", J. Am. Chem. Soc. 125, pp. 3420-3421, 2003.
Wallace et al., "Colorimetric Detection of Chemical Warfare Simulants", New J. Chem., 29, pp. 1469-1474, Sep. 22, 2005.
Wallace et al., "Detection of Chemical Warfare Simulants by Phosphorylation of a Coumarin Oximate", Chem. Commun., pp. 3886-3888, Sep. 1, 2006.
Burnworth et al., "Fluorescent Sensors for the Detection of Chemical Warfare Aggents", Chem. Eur. J., 13, pp. 7828-7836, 2007.
International Preliminary Report on Patentability with Written Opinion PCT/US2006/061865, 6 pages, Jun. 19, 2008.
Notification of Transmittal of the International Search Report and Written Opinion, PCT/US2006/061865, 9 pages, Mailing Date Feb. 5, 2008.

* cited by examiner

*Primary Examiner* — Robert Xu
(74) *Attorney, Agent, or Firm* — Baker Botts L.L.P.

(57) ABSTRACT

Compositions for detection of chemical warfare agents that comprise oximate anion reactive sites and fluorophore cores. Methods for detecting a chemical warfare agents that comprise providing a detector molecule comprising an oximate anion reactive site and a fluorophore core and detecting fluorescence from the detector molecule. Methods for enhancing the reactivity of an oximate nucleophile that comprise introducing an oxime into an aprotic solvent and deprotonating the oxime to form the oximate nucleophile with a base that creates noncoordinating anions.

1 Claim, 8 Drawing Sheets

DFP

X, Y = H, alkyl, phenyl, OH, OR, $NH_2$, $NR_2$, $NO_2$, CN, $CO_2H$, ester, amide

COMPOSITIONS AND METHODS FOR THE DETECTION OF CHEMICAL WARFARE AGENTS

RELATED PATENT APPLICATION

This application claims the benefit of U.S. provisional application Ser. No. 60/748,912 filed Dec. 9, 2005, and entitled "COMPOSITIONS AND METHODS FOR THE DETECTION OF CHEMICAL WARFARE AGENTS".

GOVERNMENT RIGHTS

This invention was made with government support under DE015017 awarded by The National Institute of Health. The government has certain rights in the invention.

TECHNICAL FIELD

The present invention, according to specific example embodiments, generally relates to detection of chemical warfare agents using oxime fluorophores.

BACKGROUND

It is well established that many organophosphorus compounds are powerful neurotoxic agents that inhibit acetylcholinesterase (AchE) by the process of phosphorylation. A particularly dangerous class of organophosphorous compounds is the phosphoryl fluoride containing species. Two such species are the chemical warfare agents (CWA) sarin (isopropyl methylphosphonofluoridate) and soman (pinacolyl methylphosphonofluoridate), referred to as GB and GD agents, respectively. For obvious safety reasons, CWA may be modeled using a chemical warfare agent simulant. Common CWS are diisopropyl fluorophosphate (DFP) and diethyl chlorophosphate (DCP).

There has been a significant interest in the decontamination and detection of CWA over the last five decades, with a large focus on phosphorylfluoride nerve agents e.g., Sarin and Soman. Chemical detection of CWA has been a long-term ambition for many researchers, even more so in this day and age due to the continuing global threat of terrorist activity. One approach that has been studied uses chromogenic detector reagents, which directly bind to a target nerve agent causing a modulation in the emitted UV-Vis wavelength. However, there are limitations in the colorimetric systems developed thus far, including low sensitivity and slow response times.

One current method for detecting CWA produces a dramatic spectral change created in response to the cyclization of a flexible chromophore. See S. W. Zhang & T. Swager, J. Am. Chem. Soc. 125, 3420 (2005). The system creates a rigid and highly conjugated fluorophore on the addition of DFP, causing an "off-on" response in the micromolar concentration range. However, the system utilizes an alcohol as a nucleophile, and hence the rate of reaction with DFP, let alone that anticipated with sarin/soman, is quite slow (half-life approaching an hour).

DRAWINGS

A more complete understanding of this disclosure may be acquired by referring to the following description taken in combination with the accompanying figures in which.

The patent or application file contains at least one drawing executed in color. Copies of this patent or patent application publication with color drawing(s) will be provided by the Office upon request and payment of the necessary fee.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed, but on the contrary, this disclosure is to cover all modifications and equivalents as defined by the appended claims.

DESCRIPTION

These fluorophores may be capable of detecting chemical warfare agents (CWA), such as phosphoryl fluoride nerve agents, at low concentrations. Accordingly, the fluorophores of the present disclosure may be used in application such as detection of CWA for military and civilian protection. Such fluorophores also may be used, among other things, in systems and methods for detecting chemical agents. As used herein, the term "chemical warfare agent" includes chemical warfare simulant.

Figure 10:
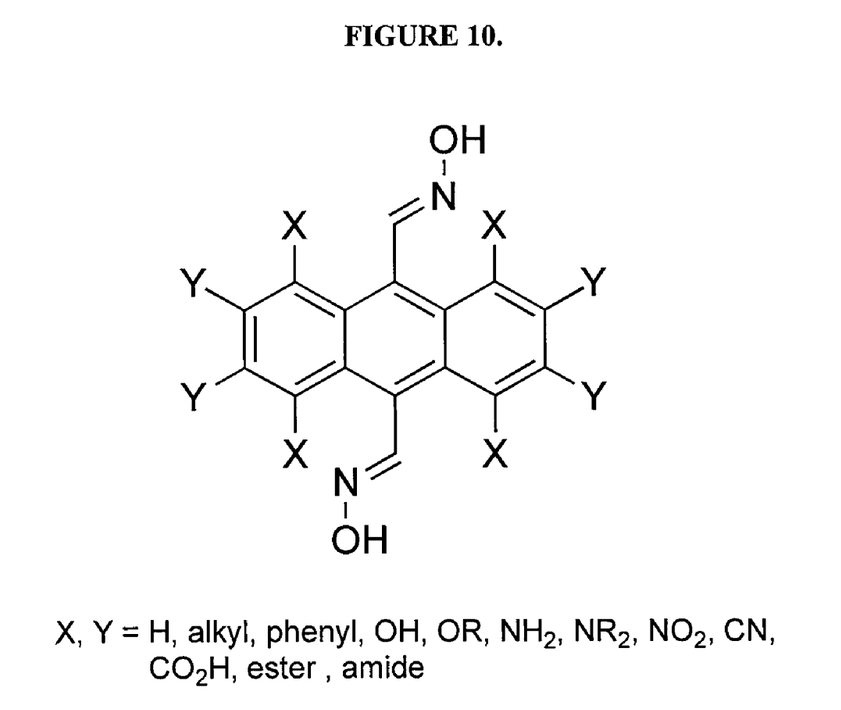
FIG. 10 shows an example of the chemical structure of an example oxime fluorophore with a substituted anthracene fluorophore core.

The fluorophores of the present disclosure generally comprise a fluorophore core having an oximate anion as the reactive site. Such fluorophores may be referred to as "oxime fluorophores." A fluorophore is a component of a molecule which causes the molecule to be fluorescent. Fluorophore cores suitable for use in the present invention include, but are not limited to, coumarin, fluorescein, substituted fluoresceins (e.g., esosine), dansyl, rhodamine, anthracene, substituted anthracenes (e.g., 9,10-diphenyl anthracene), pyrenes, and bodipy. One example of a oxime fluorophore with a substituted anthracene fluorophore core is shown in FIG. 10.

An oximate anion ($RNO^-$) belongs to a class of nucleophiles called "super nucleophiles." A super nucleophile is a reactive species in which an atom containing an unshared electron pair, typically a nitrogen or oxygen atom, is adjacent to the nucleophilic center. This increases the nucleophilicity of the reactive center, a phenomena commonly known as the α-effect. Oximate reactive sites can react with the phosphorus (V) center of a CWA. Generally, the oximate anion is formed via the deprotonation of the oxime (RNOH). Formation of the oximate anion may be carried out by any base strong enough to deprotonate the oxime. In some embodiments, bases that form noncoordinating counterions may be used to deprotonate the oxime. Bases that from noncoordinating counterions may, among other things, enhance the rate of reaction between the oximate anion and the CWA. Examples of suitable bases that form noncoordinating counterions include, but are not limited to, 1,8-Diazabicyclo[5.4.0]undec-7-ene ("DBU"); 1-tert-Butyl-4.4.4.-tris(dimethylamino)-2,2-bis[tris(diethylamino)-phosphoranylidenamino]-$2^5,4^5$-catenadi(phosphazene) ("$P_4$-t-Bu"); 2,8,9-Trimethyl-2,5,8,9-tetraaza-1-phosphabicyclo[3,3,3]undecane ("Verkade base"); and the like.

Figure 1:
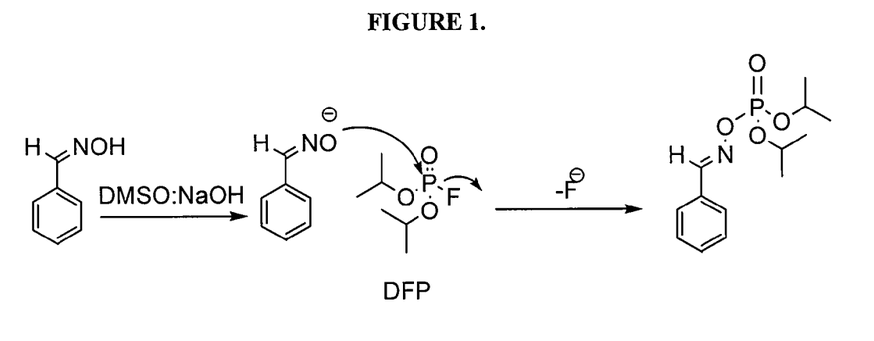
FIG. 1 shows an example of a reaction mechanism.
Figure 2:
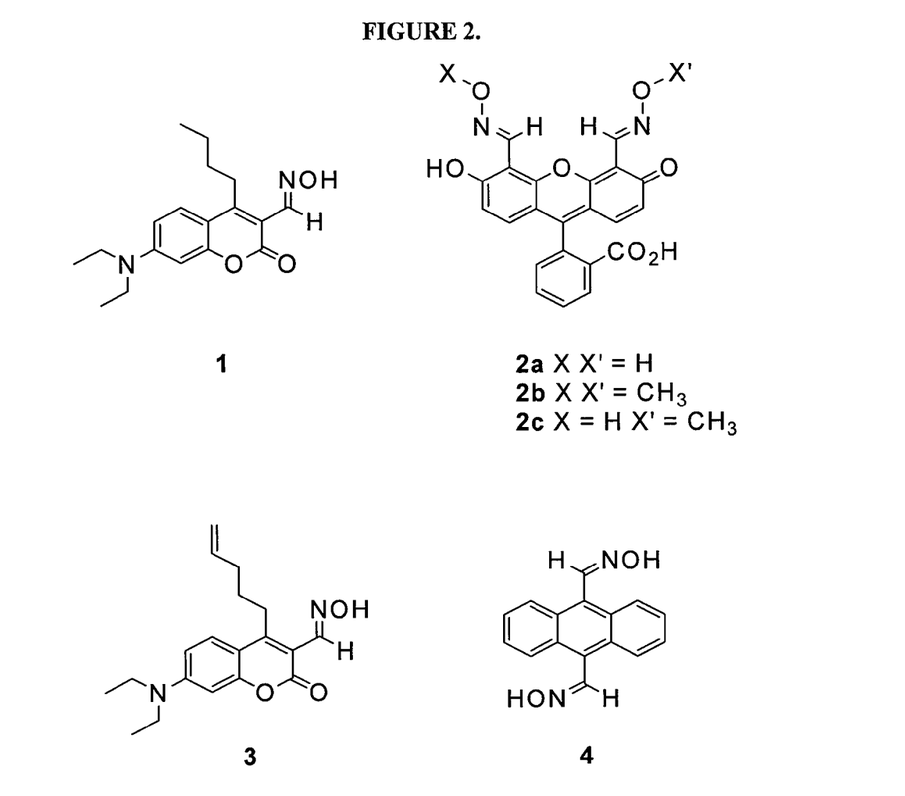
FIG. 2 shows the chemical structures of certain fluorophores.
Figure 3A:
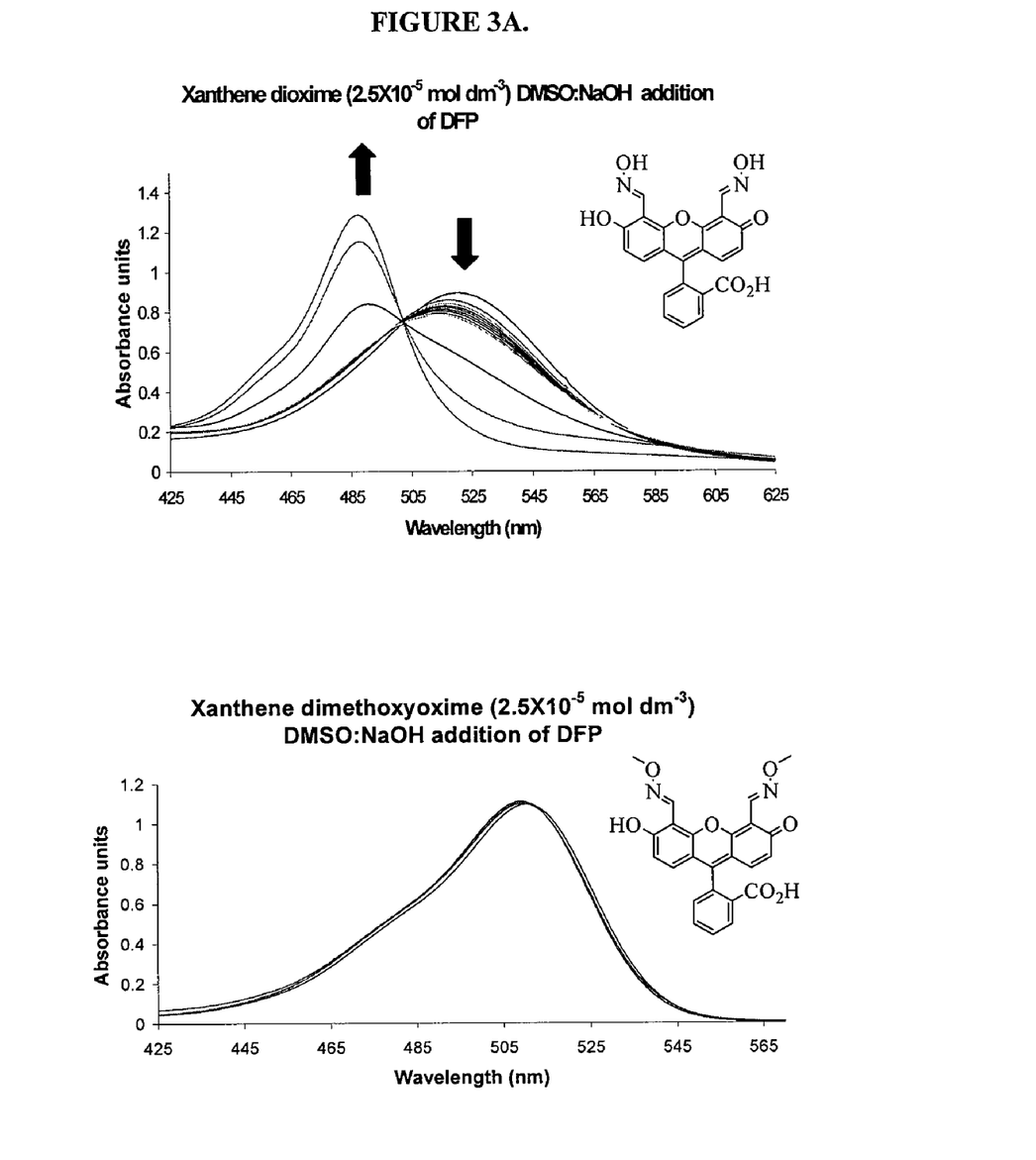
FIG. 3A shows the UV-Vis and fluorescence spectra of certain example fluorophores.
Figure 3B:
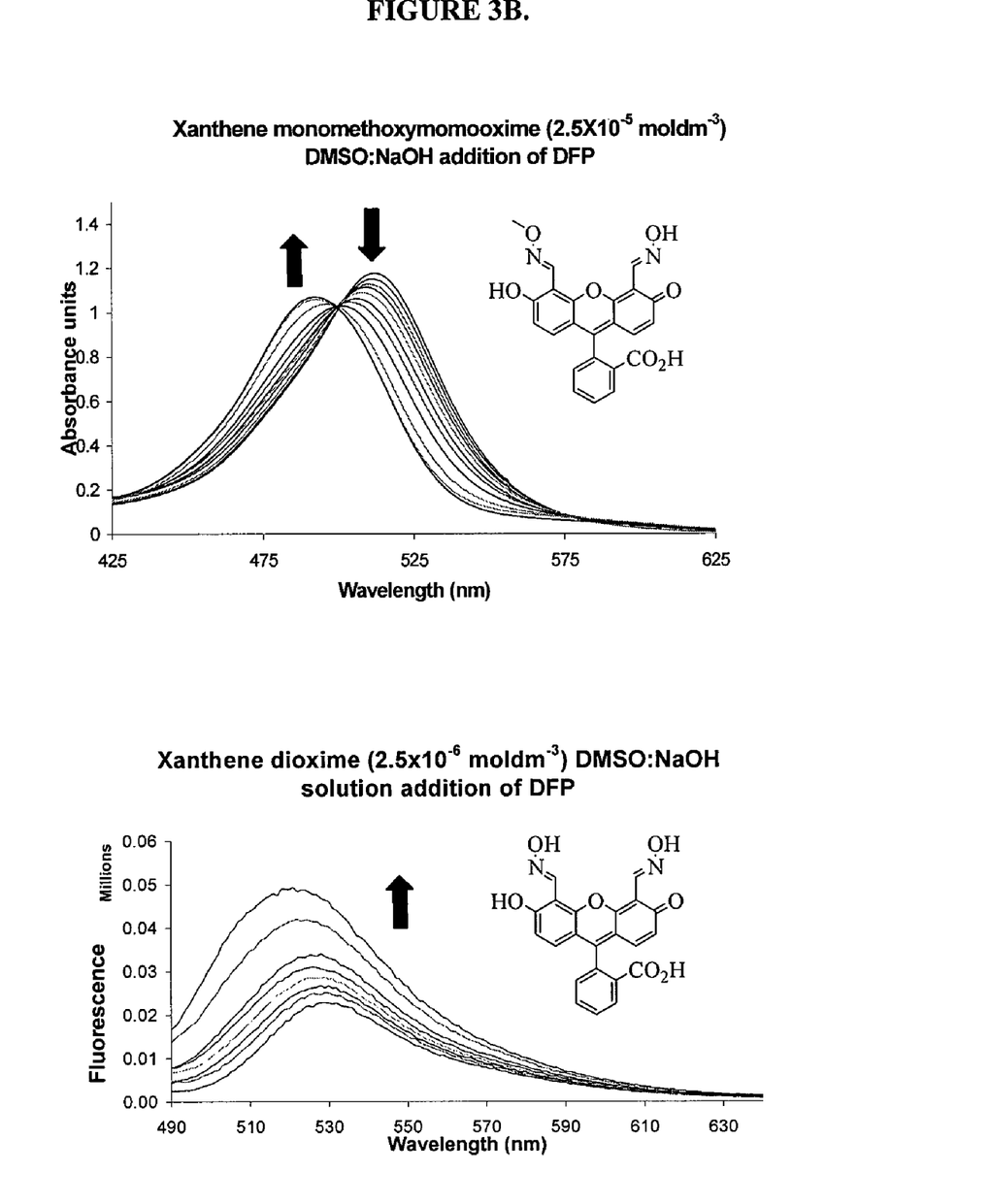
FIG. 3B shows the UV-Vis and fluorescence spectra of certain example fluorophores.
Figure 4:
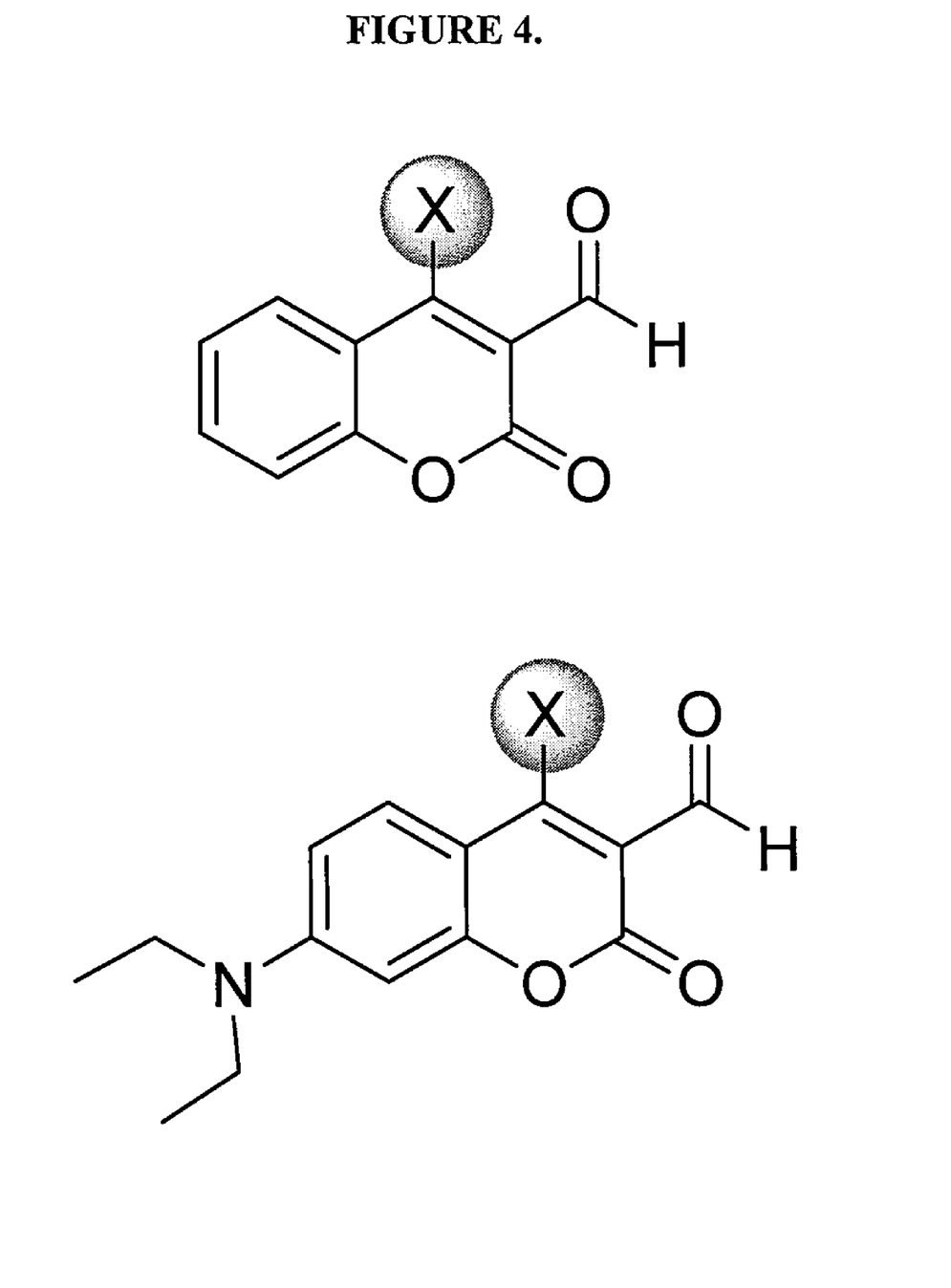
FIG. 4 shows two examples of the chemical structure of a coumarin scaffold.
Figure 5:
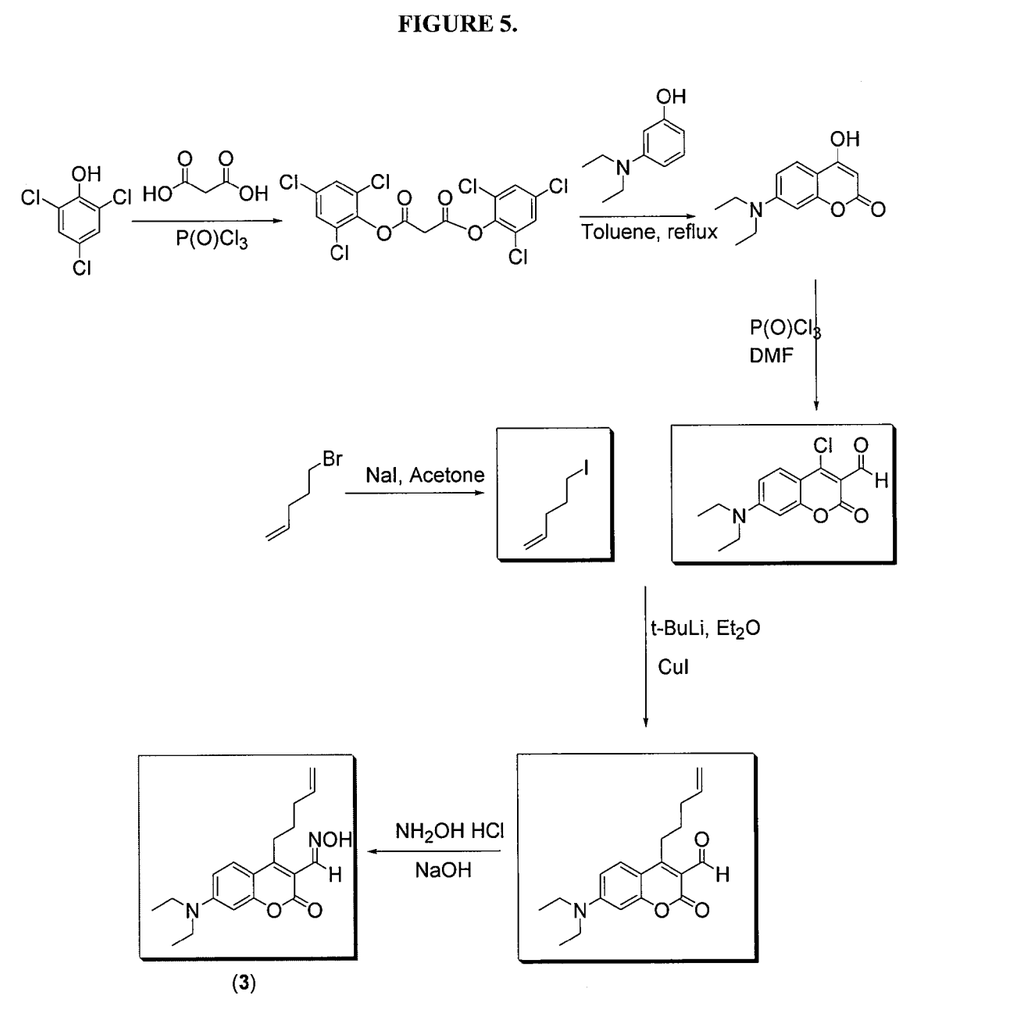
FIG. 5 shows an example of a synthesis scheme for an example fluorophore.
Figure 6:
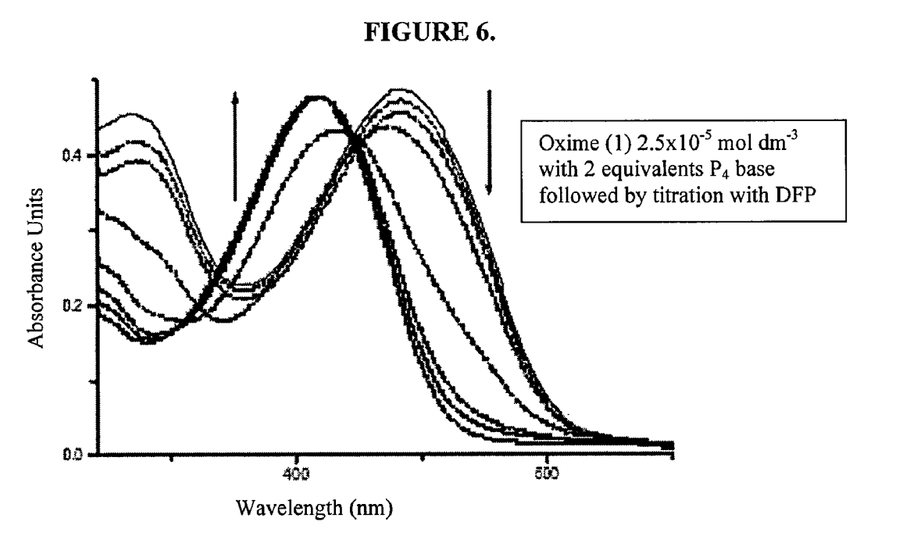
FIG. 6 shows the UV-Vis spectra of an example fluorophore.
Figure 7:
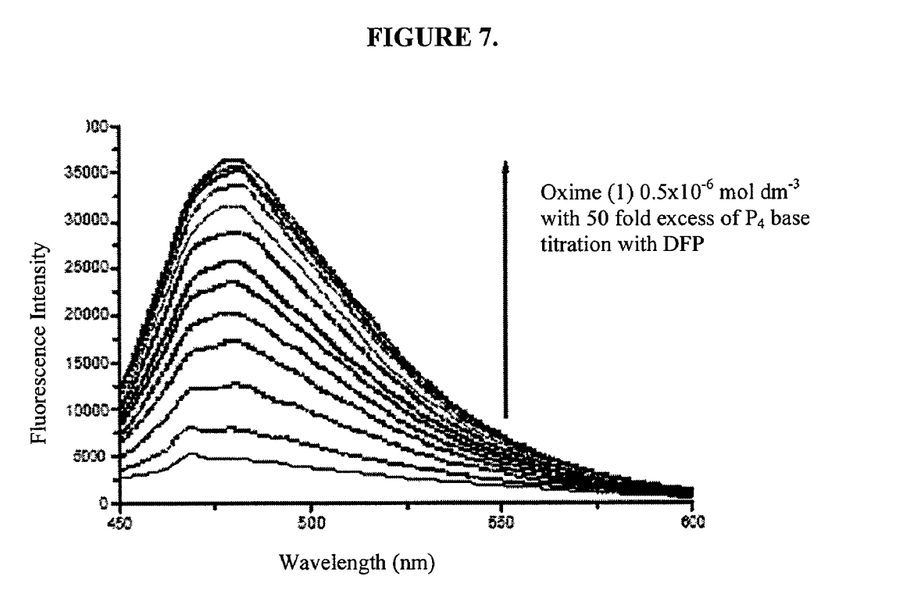
FIG. 7 shows the fluorescence spectra of an example fluorophore.
Figure 8:
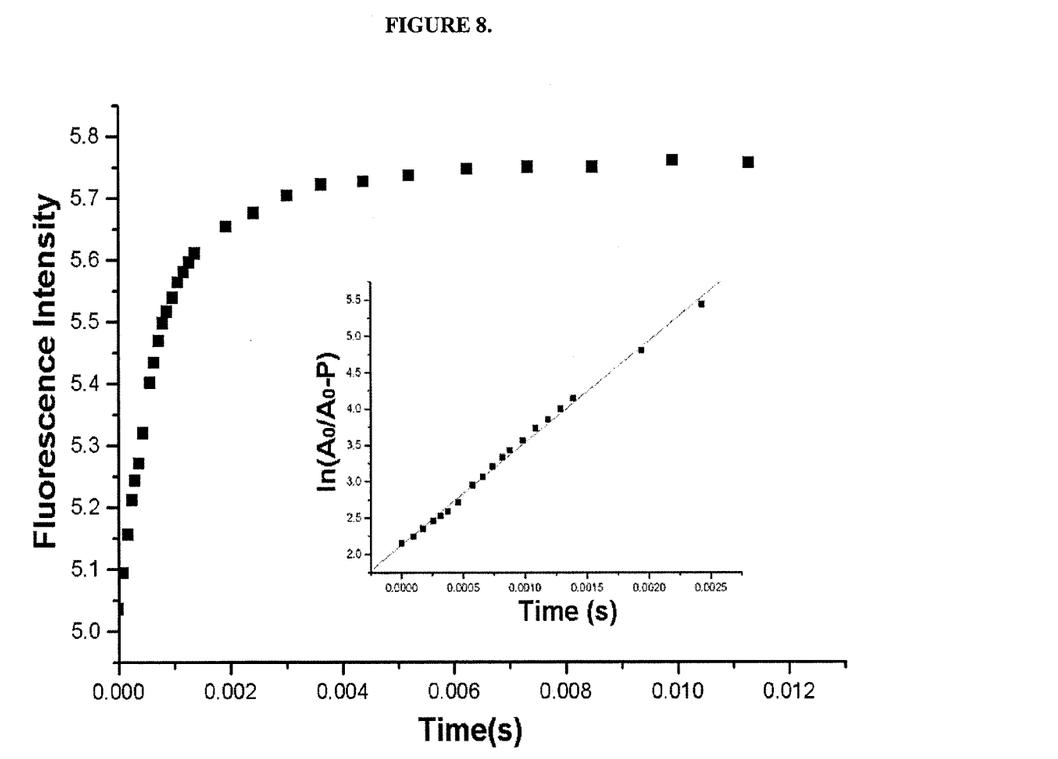
FIG. 8 shows a graph of fluorescence intensity versus time for an example fluorophore.
Figure 9:
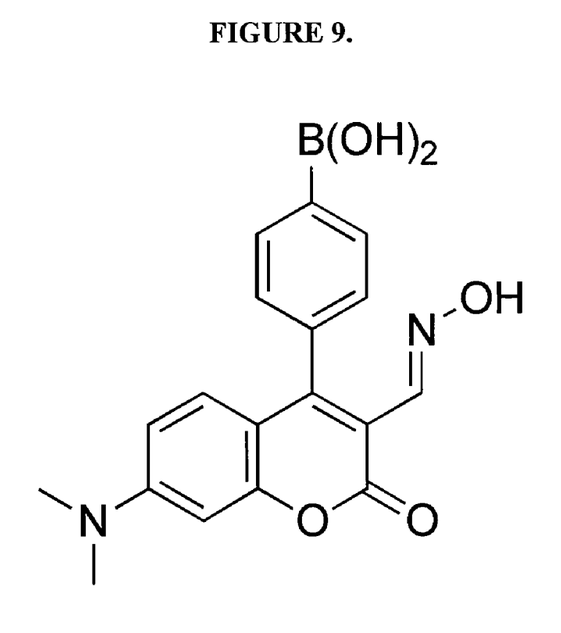
FIG. 9 shows an example of the chemical structure of an example oxime fluorophore with a Lewis-acid attached.

When oxime fluorophores are deprotonated to form the oximate anion, the high energy lone pair orbitals of the oximate anion may quench fluorescence of the oxime fluorophore via a photoinduced electron transfer (PET) mechanism. In operation, the oxime fluorophores may then be "turned-on" when a chemical agent such as a CWA is added. Upon phosphorylation by a CWA, the energy of these orbitals may be dramatically lowered, thereby reducing the PET quenching effect and turning on the fluorescence. The general reaction mechanism between an oximate and DFP is shown in FIG. 1. In some embodiments, the strength of the fluorescence signal may be increased by attaching an amino group to the fluorophore core. Suitable amino groups include, but are not limited to, a primary amino group ($NH_2$), a dimethyl amino group ($N(CH_3)_2$), and a diethyl amino group ($N(CH_2CH_3)_2$).

The kinetics of the phosphorylation reaction may be increased by incorporating into the fluorophores a second functional group that has a high affinity for fluoride, i.e., a fluoride scavenger moiety. This may overcome the slower kinetics caused by the strength of the phosphorous-fluoride bond. For example, an average P—Cl bond dissociation energy is 326 KJ/mol, while that for P—F is 490 KJ/mol. Typical fluoride scavenger moieties are Lewis acidic groups such as boronates and pseudo-Lewis acid moieties such as silanes. An example of an oxime fluorophore with a Lewis-acid attached is shown in FIG. 9. The silyl group is excellent in scavenging fluoride, in that this is the common procedure for silyl group deprotection. In some embodiments, a fluoride scavenger moiety such as silver may be added to a solution containing the oxime fluorophore. By way of explanation, and not of limitation, the fluoride scavenger moiety may coordinate the P—F bond prior to nucleophilic attack to weaken the bond enough to accomplish rapid detection. A reduction of the half-life to seconds only requires approximately a 12 to 17 KJ/mol reduction in activation energy for oximate attack.

Examples of certain oxime fluorophores of the present disclosure are shown in FIG. 2 (compounds 1-2a,2c-4). Such oxime fluorophores may be synthesized using known procedures of synthetic organic chemistry, such as, for example, the synthetic procedures described in K. J. Wallace, et al., "Colorimetric detection of chemical warfare simulants," New J. Chem. 29 1469-74 (2005).

In some embodiments, a method for enhancing the reactivity of an oximate nucleophile comprises: introducing the oxime fluorophore into an aprotic solvent and adding a base to deprotonate the oxime fluorophore to form the oximate, wherein the base forms a noncoordinating counterion. Embodiments of this type may be said to create a "naked" nucleophile, thereby increasing the nucleophilicity and the rate of reaction. Suitable aprotic solvents may be polar or nonpolar. Examples of suitable solvents include, but are not limited to, DMF, DMSO, acetonitrile, and THF. Examples of suitable bases include, but are not limited to, DBU, $P_4$-t-Bu, and Verkade base.

To facilitate a better understanding of the present invention, the following examples of specific embodiments are given. In no way should the following examples be read to limit or define the entire scope of the invention.

EXAMPLES

To study certain oxime fluorophores of the present disclosure, a UV-Vis absorbance spectral change needed to be observed. Accordingly, certain example oxime fluorophores may include a nitro moiety as a UV-Vis 'handle'.

Specific example embodiments of oxime fluorophores may react with sarin/soman chemical warfare simulant in less than about 5 seconds in DMSO, resulting in large emission intensity and wavelength shifts. Fluorescein bisoxime (FIG. 2, compound 2a) and fluorescein monooxime (FIG. 2, compound 2c) both undergo an absorbance shift (a hypsochromic shift) when treated with DFP. See FIG. 1. As a control, a diprotected species (FIG. 2, compound 2b) was synthesized; and for this species, no spectral change was observed. The fluorescence signal of (FIG. 2, compound 2a) is turned off under basic conditions. This may be due to the lone pair quenching by the super nucleophile, as a consequence of the PET mechanism. A fluorescence signal is subsequently 'turned-on' by the addition of DFP. The UV-Vis and fluorescence spectra for compounds 2a-2c of FIG. 2 are shown in FIG. 3.

Other specific example embodiments of oxime fluorophores are shown in FIG. 2, compounds 1 and 3. These compounds have a coumarin scaffold (two examples are shown in FIG. 4), and many functional groups can be appended to the coumarin scaffold in the four-position. One example of a suitable synthesis for compound 3 of FIG. 2 is shown in FIG. 5.

The specific example oxime fluorophore shown in FIG. 2, compound 1 was studied to elucidate some UV-Vis and fluorescence properties. UV-Vis studies were carried out by preparing a solution of compound 1 (FIG. 2) in DMSO ($2.5\times10^{-5}$ mol $dm^{-3}$). The initial UV-Vis spectra showed a broad band at $\lambda_{max}$=409 nm, assigned to the n-$\pi^*$ transition. Upon addition of $P_4$-t-Bu ($^{DMSO}pK_{BH}+$=30.25) solution, a bathochromoic shift in wavelength to $\lambda_{max}$=443 nm was observed (shown in FIG. 6), typical of anionic species in solution. On the addition of DFP (6.0 mol $dm^{-3}$ in DMSO) the absorbance intensity is hypsochromically shifted to $\lambda_{max}$=409 nm (shown in FIG. 6).

The compound 1 of FIG. 2 is also highly fluorescent, and the fluorescence signal is turned off under basic conditions. This may be due to PET quenching by the lone pair of the oximate anion. A fluorescence signal is subsequently "turned-on" by the addition of DFP, as shown in FIG. 7. Fluorescence studies ($\lambda_{ex}$=410 nm) were carried out by preparing a $0.5\times10^{-6}$ mol $dm^{-3}$ solution in DMSO with a 50 fold excess of $P_4$ base, and titrating small aliquots of DFP. FIG. 7 shows the fluorescence signal of compound 1 with the $P_4$-t-Bu base alone shows to be a weak fluorescence signal. The fluorescence signal increases with the addition of DFP.

Stop-flow kinetics experiments were carried out by watching the "turn on" of the fluorescence signal upon the addition of DFP. A $2.5\times10^{-5}$ mol $dm^{-3}$ of compound 1 of FIG. 2 was prepared in DMSO with the $P_4$-t-Bu base. A 1.25×10 mol $dm^{-3}$ of DFP was prepared in DMSO. One milliliter of each solution was transferred to a separate syringe and placed in the stop-flow apparatus. Equal volumes of the solutions were mixed together and the reaction was monitored for 1 second. The fluorescence intensity increased upon mixing, in good agreement with the fluorescence studies described above. By monitoring the fluorescence intensity at various times one can calculate the rate of the reaction by plotting $\ln(A_o/(A_o-P))$ versus time (FIG. 8 inset). Where $A_o$ is the final fluorescence intensity and P is the fluorescence intensity at each time interval measured. The rate constant k (slope) was calculated to be $1410\ s^{-1}$. Therefore the half-life $(t_{1/2})=\ln(2)/k$, is calculated to be approximately 50 ms.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

Therefore, the present invention is well adapted to attain the ends and advantages mentioned as well as those that are inherent therein. While numerous changes may be made by those skilled in the art, such changes are encompassed within the spirit of this invention as illustrated, in part, by the appended claims.

What is claimed is:

1. A composition for detection of a chemical warfare agent comprising a compound represented by the following formula:

wherein X is a structure represented by

* * * * *